(12) United States Patent
Sun et al.

(10) Patent No.: US 9,248,107 B2
(45) Date of Patent: Feb. 2, 2016

(54) VACCINE STABILIZER

(75) Inventors: Tianxiao Sun, Lexington, MA (US); Philip M. Levesque, Nashua, NH (US); Alicja T. Brown, Silver Spring, MD (US); Cynthia K. Lee, Washington, DC (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 640 days.

(21) Appl. No.: 13/355,158

(22) Filed: Jan. 20, 2012

(65) Prior Publication Data

US 2012/0201849 A1  Aug. 9, 2012

Related U.S. Application Data

(63) Continuation of application No. PCT/US2010/043019, filed on Jul. 23, 2010.

(60) Provisional application No. 61/229,153, filed on Jul. 28, 2009.

(51) Int. Cl.

| | | |
|---|---|---|
| A61K 47/18 | (2006.01) | |
| A61P 31/12 | (2006.01) | |
| A61K 39/12 | (2006.01) | |
| A61K 47/42 | (2006.01) | |
| A61K 39/00 | (2006.01) | |
| A61P 37/04 | (2006.01) | |
| A61K 31/13 | (2006.01) | |
| A01N 1/02 | (2006.01) | |
| A61K 47/02 | (2006.01) | |
| A61K 9/00 | (2006.01) | |
| A61K 47/26 | (2006.01) | |

(52) U.S. Cl.
CPC ............ *A61K 31/13* (2013.01); *A01N 1/021* (2013.01); *A61K 9/0019* (2013.01); *A61K 47/02* (2013.01); *A61K 47/18* (2013.01); *A61K 47/183* (2013.01); *A61K 47/26* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 5,580,856 A | 12/1996 | Prestrelski et al. | |
| 6,051,238 A * | 4/2000 | Volkin et al. | 424/212.1 |
| 2005/0032183 A1 | 2/2005 | Osslund et al. | |
| 2007/0111231 A1 * | 5/2007 | Magness et al. | 435/6 |
| 2007/0243185 A1 | 10/2007 | Gombotz et al. | |
| 2007/0259334 A1 * | 11/2007 | Truong-Le et al. | 435/4 |
| 2008/0166784 A1 | 7/2008 | Chen et al. | |
| 2012/0201849 A1 * | 8/2012 | Sun et al. | 424/204.1 |

OTHER PUBLICATIONS

Gaucher et al. (Journal of Experimental Medicine; 205 (13): 3119-3131).*
Monath. Development of Biological Standards. 1996; 87: 219-225, abstract only).*
Post et al. (Memorial Institute of Oswaldo Cruz. Rio de Janeiro. 1991; 86 (2): 239-246).*
Barrett, Alan DT. "Current status of flavivirus vaccines." Annals of the New York Academy of Sciences 951.1 (2001): 262-271.*
Baskakov et al. (Journal of Biological Chemistry. 278 (9): 4831-4834).*
Arakawa, T., et al., Advanced Drug Delivery Reviews, vol. 10, No. 1, 1993, pp. 1-28.
European Search Report Mailed Apr. 3, 2014 Issued on Corresponding EP Application No. 10804910.7.

* cited by examiner

*Primary Examiner* — Shanon A Foley

(57) ABSTRACT

Disclosed herein is a formulation capable of enhancing thermostability and shelf-life of a biological product, the formulation comprising: a tertiary amine N-oxide or a derivative thereof represented by the formulae:

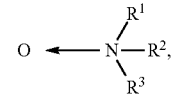

wherein $R^1$, $R^2$, and $R^3$ may be identical or different and each is a straight or branched lower alkyl group having from 1 to 4 carbon atoms; an inorganic salt; glutamic acid or a salt thereof; a polyol; a physiologically acceptable buffer, and a pharmaceutically acceptable carrier. The tertiary amine N-oxide may be trimethylamine-N-oxide, $(CH_3)_3NO$. The formulation is useful for vaccine stabilization.

16 Claims, 1 Drawing Sheet

Stability of YF 17D virus adsorbed to alum in different formulation buffers, evaluated after 4, 7 and 12 days at 37°C

VACCINE STABILIZER

RELATED APPLICATIONS

This application is a continuation of International Application No. PCT/US2010/043019, which designated the United States and was filed on Jul. 23, 2010, published in English, which claims priority to U.S. Provisional Patent Application No. 61/229,153, filed on Jul. 28, 2009. The entire teachings of the above applications are incorporated herein by reference.

FIELD OF INVENTION

This invention relates to a compositions and methods capable of stabilizing a biological product, such as, for example, a vaccine formulation.

BACKGROUND

A biological product, as the term is used herein, is a product that may be prepared using living organisms. For example, virus or bacteria may be produced for use in vaccines by using live tissue cells as a substrate. Humulin is another biological product; it is synthesized in a non-disease-producing strain of *Escherichia coli* bacteria that has been genetically altered to produce human insulin.

Most biological products are prone to degradation such as thermal, photochemical, or oxidative degradation. Because biological products such as vaccines and insulin need to be distributed worldwide, and because ambient temperatures in different regions vary greatly, there exists a need to stabilize vaccine and other biological preparations for transportation and use. Several stabilization methods for vaccines have been used in the past.

One strategy has been the use of very low temperatures, for example, −10 degrees Celsius (−10° C.) to −70 degrees Celsius (−70° C.). However, lack of availability of facilities for such low temperature storage limits the practicality of this approach.

Another method is lyophilization, an expensive procedure. Lyophilised vaccines are reasonably stable and can be stored at about 4° to 8° C. However, because the lyophilized vaccine must be reconstituted prior to use, the liquid, reconstituted preparation loses potency while standing at room temperature. This can result in insufficient titer to confer immunity and may therefore result in the failure of an immunization program.

The use of chemical stabilizers added to the vaccine has been yet another approach. The stabilizers are used in conjunction with either lower temperature storage or lyophilization methods. However, none of the available stabilizers imparts the desired enhanced sustained level of stability. Further, many of these chemical stabilizers, such as albumin, and gelatin, are of animal origin, and carry a risk that vaccines in which these stabilizers are incorporated may be contaminated with various agents of animal origin. Such contaminants may carry a risk of an allergic reaction in the patient receiving the vaccine, and may also cause batch to batch variability in the vaccines stabilized with animal origin chemicals.

Thus, there is an on-going need for an improved chemical stabiliser for liquid and lyophilized viral vaccines and other biological products. There is also a need for improved lyophilized or liquid viral vaccines having prolonged storage stability over a range of temperatures, and having diminished reduction in titer. There is a further need to enhance the immunological activity of vaccine preparations.

BRIEF SUMMARY OF THE DISCLOSURE

In contrast to prior art compositions and methods for stabilizing biological products, the inventors of the present subject matter have now discovered a new stabilizing formulation and related method that are capable of enhancing thermostability and shelf life of various biological products.

One embodiment of the invention is a formulation capable of enhancing thermostability and shelf-life of a biological product, the formulation comprising: a tertiary amine N-oxide or a derivative thereof represented by the formulae:

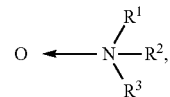

wherein $R^1$, $R^2$, and $R^3$ may be identical or different and each is a straight or branched lower alkyl group having from 1 to 4 carbon atoms; an inorganic salt; glutamic acid or a salt thereof; a polyol; a physiologically acceptable buffer, and a pharmaceutically acceptable carrier.

In a preferred embodiment of the formulation, the tertiary amine N-oxide is trimethylamine-N-oxide, $(CH_3)_3NO$.

Another embodiment of the invention is a vaccine comprising an inactivated or attenuated virus, an adjuvant, and a stabiliser comprising from about one millimolar to about 50 millimolar magnesium chloride, $MgCl_2$; from about 8 millimolar to about 200 millimolar glutamic acid; from about 0.05 millimolar to about 2.5 millimolar mannitol; from about one millimolar to about 500 millimolar trimethylamine-N-oxide; and an amount of a physiologically acceptable buffer effective to adjust or maintain the pH at from about 6.5 to about 8.5, and preferably to about 7.5.

Yet another embodiment of the invention is a formulation capable of enhancing thermostability and shelf-life of a biological product, the formulation comprising: from about one millimolar to about 200 millimolar glutamic acid; from abut 0.05 millimolar to about 5 millimolar mannitol; from about 0.01 milligram per milliliter to about 0.1 milligram per milliliter protamine, and from about 0.01 percent to about 1 percent dextrose, and an amount of a physiologically acceptable buffer effective to adjust or maintain the pH at from about 6.5 to about 8.5, and preferably to about 7.5.

The invention also relates to a formulation comprising: an inactivated virus or an attenuated virus; alum; trimethylamine-N-oxide; mannitol; glutamic acid; magnesium chloride, MgCl2; sodium chloride; and a suitable buffer to maintain the pH of the formulation at about 7.5. The formulation may comprise from about 0.1 percent (w/v) to about 0.5 percent (w/v) alum, and preferably about 0.2 percent (w/v) alum; from about 1.5 millimolar to about 20 millimolar trimethylamine-N-oxide, preferably about 2 millimolar trimethylamine-N-oxide; from about 0.05 millimolar to about 2 millimolar mannitol, preferably from about 0.1 millimolar to about 1.1 millimolar mannitol; from about 8 millimolar to about 150 millimolar glutamic acid, preferably from about 10 millimolar to about 100 millimolar glutamic acid; and from about 100 millimolar to about 500 millimolar sodium chloride, preferably from about 145 millimolar to about 500 millimolar sodium chloride.

The disclosed formulations provide unexpectedly diminished reduction in titer of vaccines and other biological products for an extended time as compared to such products incorporating currently available stabilisers. The enhanced stability of the disclosed formulations may be particularly important for liquid and lyophilised viral vaccines. Additionally, the disclosed formulations are free of most or all components of animal origin, for example, serum, albumin, and gelatin, and therefore present a lower risk of allergic reaction in an individual to whom the formulation is administered. The disclosed formulations, being substantially free of contamination that can accompany components of animal origin, and are more uniform from one batch to another than are formulations having animal origin components.

BRIEF DESCRIPTION OF THE DRAWING

The FIGURE is a graph showing the stability of YF 17D virus adsorbed to alum in different stabilisation formulations according to an embodiment of the invention, evaluated after 4, 7 and 12 days at 37° C.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including the accompanying claims and abstract, and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including the accompanying claims and abstract), or to any novel one, or any novel combination, of the steps of any method or process so disclosed.

The inventors of the disclosed subject matter designed a study to screen for chemicals that could impart stability to an inactivated virus in solution, in particular, to an alum-adsorbed yellow fever virus. Following high throughput screening, many combinations were selected for testing. From those, certain combinations produced an unexpected, significant increase in stability. Some of the components of the disclosed formulation have, to the best of the inventors' knowledge, never been used previously for stabilising biological formulations, in particular, vaccine formulations.

Disclosed herein is a formulation capable of enhancing thermostability and shelf-life of a biological product, the formulation comprising: a tertiary amine N-oxide or a derivative thereof represented by the formulae:

$$O \leftarrow N{\overset{R^1}{\underset{R^3}{-}}}R^2,$$

wherein $R^1$, $R^2$, and $R^3$ may be identical or different and each is a straight or branched lower alkyl group having from 1 to 4 carbon atoms; an inorganic salt; glutamic acid, $HOOC(CH_2)_2CH(NH_2)COOH$ or a salt thereof; a polyol; a physiologically acceptable buffer, and a pharmaceutically acceptable carrier. In a preferred embodiment of the formulation, the tertiary amine N-oxide is trimethylamine-N-oxide, $(CH_3)_3NO$.

The term "lower alkyl group," as used herein to describe $R^1$, $R^2$, and $R^3$ in the above formula, denotes alkyl groups having 1-4 carbon atoms. For example, $R^1$, $R^2$, and $R^3$ may each be chosen independently from a methyl, an ethyl, a propyl, an n-butyl, and an isobutyl group.

In one embodiment of the disclosed formulation, the inorganic salt is magnesium chloride, $MgCl_2$. In various embodiments of the invention, the polyol may be a C3 to a C8 polyol, for example, mannitol, $C_6H_8(OH)_6$.

The concentration of trimethylamine-N-oxide may be from about 1.5 millimolar (mM) to about 800 mM, or from about 2 mM to about 600 mM, or typically from about 2.0 mM to about 20 mM.

The concentration of magnesium chloride ($MgCl_2$) may be from about 0.8 mM to about 80 mM, or from about 5 mM to about 50 mM, and typically from about 1 mM to about 12 mM.

The concentration of glutamic acid may be from about 5 mM to about 500 mM, or from about 7 mM to about 300 mM, and typically from about 8 mM to about 100 mM.

The concentration of mannitol may be from about 0.01 percent (w/v) to about 5 percent (w/v), or from about 0.01 percent to about one (1) percent, or typically about 0.02 percent. As the term is used herein, "w/v" refers to the concentration of a solution expressed as a "weight/volume percentage" or percentage solution. The percentage is calculated from the weight of solute in grams (g), divided by the total volume of solution in milliliters (mL). The concentration of mannitol may be from about 0.05 mM to about 2 mM in a vaccine formulation or in a stabiliser solution, each according to an embodiment of the invention, and preferably from about 0.11 mM to about 1.1 mM.

The physiologically acceptable buffer may be present in an amount effective to adjust or maintain the pH at from about 6.5 to about 8.5, or from about 7.0 to about 8.0, and typically about 7.5. A suitable buffer may be a tris buffer, for example, Tris HCl, also known as: 2-Amino-2-(hydroxymethyl)-1,3-propanediol, hydrochloride; and Tris(hydroxymethyl)aminomethane Hydrochloride; or a phosphate buffer. However, those of skill in the chemical or biochemical arts may, without undo experimentation, determine that another buffer system is suitable for use in an embodiment of the invention.

A preferred embodiment of the invention is a vaccine formulation comprising an inactivated or an attenuated virus, such as, for example, a yellow fever virus, the vaccine formulation comprising from about 1.2 millimolar (mM) to about 12 millimolar (mM) magnesium chloride ($MgCl_2$), from about 10 mM to about 100 mM glutamic acid, from about 0.1 mM to about 1.1 mM mannitol, and from about 2.0 mM to about 20 mM trimethylamine-N-oxide, and an amount of a physiologically acceptable buffer effective to adjust and/or maintain the pH at from about 6.5 to about 8.5, or preferably from about 7.0 to about 8.0.

The inventors of the present subject matter also discovered that protamine is an effective addition to a stabilising formulation for biological products. For example, in another embodiment of the invention, a formulation capable of enhancing thermostability and shelf-life of a biological product comprises: from about one millimolar to about 200 millimolar glutamic acid, from abut 0.05 mM to about 5 mM mannitol, from about 0.01 milligram per milliliter to about 0.1 milligram per milliliter protamine, and from about 0.01 percent to about 1 percent dextrose, and an amount of a physiologically acceptable buffer effective to adjust or maintain the pH at from about 6.5 to about 8.5, and preferably about 7.5. The concentration of protamine may also be from about 0.005 milligram to about 0.2 milligram. The concentration of the other components in the protamine-based formulation may be, for example, as disclosed above for the formulation based on trimethylamine-N-oxide.

Any of the disclosed formulations may comprise an adjuvant such as aluminum hydroxide.

Any of the disclosed formulations may be suitable for extending the shelf life and/or the efficacy of insulin.

Any of the disclosed formulations may be suitable for a biological product comprising an inactivated virus, an attenuated virus, a live virus, and combinations thereof. An inactivated virus or an attenuated virus suitable for use with the formulation may be a yellow fever virus. The biological product may comprise a single bacteria or more than one bacteria, or a combination of bacteria and one or more viruses.

Various embodiments of the disclosed formulation can apply to the stabilization of biological compositions including vaccines intended for use by any species, including, for example, human, feline, canine, equine, porcine, bovine, ovine.

Embodiments of these formulations can be used in the stabilization of proteins, including recombinant proteins, liquid enzyme compositions, and viral-delivered vectors, for example.

As used herein, the term "vaccine" may refer in general to a suspension of live, attenuated, or inactivated (killed) microorganisms such as viruses, bacteria, rickettsiae, or of other antigens such as antigenic proteins and other substances derived from them, administered for prevention, amelioration, or treatment of infectious diseases.

An attenuated vaccine is a vaccine prepared from live microorganisms or viruses subjected to adverse conditions leading to loss of their virulence but retention of their ability to induce protective immunity. An attenuated vaccine is also known as a "replicative vaccine" because it contains organisms that are able to reproduce.

A formulation according to an embodiment of the invention may be an acellular vaccine, a cell-free vaccine prepared from purified antigenic components of cell-free microorganisms, carrying less risk than whole-cell preparations.

An example of such a "cell-free vaccine" is anthrax vaccine, a cell-free protein extract of cultures of *Bacillus anthracis*, used to immunize against anthrax. Another example is a "subunit vaccine," which is a vaccine containing no viral nucleic acid, and containing only small amounts of nonviral antigens derived from the culture medium. Cell-free vaccines and subunit vaccines are less likely to cause adverse reactions than a vaccine containing attenuated bacteria or a whole, attenuated or inactivated virion.

The disclosed formulation may be suitable for enhancing the stability of a vaccine preparation comprising an antigen constituent. Any of the disclosed formulation may be used in a vaccine comprising a particle chosen from a virus-like particle, a subunit, a toxoid, a plasmid, a peptide, a polypeptide, a fusion protein, a conjugated protein, a polysaccharide, a conjugated polysaccharide, a recombinant protein, a DNA, an RNA, and combinations thereof.

The disclosed formulation may enhance the stability of a biological product including an inactivated virus or an attenuated virus chosen from St. Louis encephalitis virus, Japanese encephalitis virus, tick-borne encephalitis viruses, dengue virus, Kyasanur Forest disease virus, and combinations thereof. The stability of a composition including an inactivated virus or an attenuated virus chosen from measles, mumps, rubella, varicella, polio, hepatitis A, hepatitis B, herpes simplex 1, herpes simplex 2, rabies, influenza A, influenza B, H1N1, rotavirus, and combinations thereof, may be enhanced by any of the disclosed formulations.

An embodiment of the invention is a vaccine or other biological composition including a bacteria chosen from Feline *Bordetella, Bordetella bronchiseptica*, and combinations thereof.

The disclosed formulation may be suitable for the following types of vaccines, including, without limitation: an autogenous vaccine prepared from microorganisms freshly isolated from the lesion of the patient who is to be treated with it; a BCG vaccine (the Calmette-Guérin strain of *Mycobacterium bovis*) used to immunize against tuberculosis and in treatment of bladder cancer; a cholera vaccine a preparation of killed *Vibrio cholerae*, used in immunization against cholera; diphtheria and tetanus toxoids and pertussis vaccine (DTP), a combination of diphtheria and tetanus toxoids and pertussis vaccine; used for simultaneous immunization against diphtheria, tetanus, and whooping cough; diphtheria and tetanus toxoids and pertussis vaccine adsorbed and *Haemophilus* b conjugate vaccine, a combination of diphtheria toxoid, tetanus toxoid, pertussis vaccine, and b conjugate vaccine; used for simultaneous immunization against diphtheria, tetanus, pertussis, and infection by *Haemophilus influenzae* type b; *Haemophilus* b conjugate vaccine (HbCV), a preparation of *Haemophilus influenzae* type b capsular polysaccharide covalently bound to diphtheria toxoid or to a specific diphtheria, meningococcal, or tetanus protein; *Haemophilus* b polysaccharide vaccine (HbPV), a preparation of purified capsular polysaccharide derived from *Haemophilus influenzae* type b; hepatitis A vaccine inactivated, an inactivated whole virion vaccine derived from an attenuated strain of hepatitis A virus grown in cell culture; hepatitis B vaccine, a preparation of hepatitis B surface antigen, derived either from human plasma of carriers of hepatitis B (hepatitis B v. inactivated) or from cloning in yeast cells (hepatitis B v. [recombinant]; a human diploid cell vaccine (HDCV) such as rabies vaccine; an influenza virus vaccine, for example, a trivalent vaccine containing two influenza A virus strains and one influenza B virus strain, or an H1N1 vaccine; a Lyme disease vaccine (recombinant OspA), a preparation of outer surface protein A (OspA), and a cell surface lipoprotein of *Borrelia burgdorferi*, produced by recombinant technology; a measles, mumps, and rubella virus vaccine live (MMR) a combination of live, attenuated measles, mumps, and rubella viruses; a measles and rubella virus vaccine, a combination of live, attenuated measles and rubella viruses; a measles virus vaccine live, a live, attenuated virus vaccine; a meningococcal polysaccharide vaccine, a preparation of capsular polysaccharide antigen of *Neisseria meningitidis*, used to provide immunity to meningitis; a mumps virus vaccine live;

a pertussis vaccine, a preparation of killed *Bordetella pertussis* bacilli, a whole-cell vaccine or purified antigenic components thereof (acellular vaccine), used to immunize against pertussis, but generally used in combination with diphtheria and tetanus toxoids (DTP or DTaP); a plague vaccine a preparation of killed *Yersinia pestis* bacilli; a pneumococcal heptavalent conjugate vaccine, a preparation of capsular polysaccharides from the seven serotypes of *Streptococcus pneumoniae* coupled to a nontoxic variant of diphtheria toxin; a pneumococcal vaccine polyvalent, a preparation of capsular polysaccharides from the 23 serotypes of *Streptococcus pneumoniae* causing the majority of pneumococcal disease; a poliovirus vaccine inactivated (IPV), a suspension of formalin-inactivated polioviruses used for immunization against poliomyelitis; a poliovirus vaccine live oral (OPV), a preparation of a combination of the three types of live, attenuated polioviruses; an inactivated rabies virus used for pre- and post-exposure rabies immunization; a rotavirus vaccine live oral, a live virus vaccine produced from a mixture of four rotavirus types grown in fetal rhesus diploid cells; used to immunize infants against rotaviral gastroenteritis; a rubella and mumps virus vaccine live, a combination of live attenuated rubella and mumps viruses; a rubella virus vaccine live, a live attenuated virus vaccine; Sabin vaccine (poliovirus v. live oral.); Salk vaccine (poliovirus v. inactivated); a typhoid vaccine (any of several preparations of *Salmonella typhi* used for immunization against typhoid fever, including a parenteral heat- and phenol-inactivated bacteria vaccine, an oral live vaccine prepared from the attenuated strain Ty21a, and a parenteral vaccine prepared from typhoid Vi capsular polysaccharide); and varicella virus vaccine live, a preparation of live, attenuated human herpesvirus 3 (varicella-zoster virus) used to immunize against varicella and herpes zoster.

Various embodiments of a vaccine formulation according to the invention may comprise aluminum hydroxide as adjuvant and pharmaceutical excipients such as physiological saline solution, pH-controlling agents, preservatives, organic solvents, hydrophobic agents, and surfactants.

A vaccine may be stabilized by adding to the vaccine an amount of a formulation disclosed herein effective to stabilise the vaccine. A vaccine stabilized according to any formulation disclosed herein may be administered by a method comprising administering the vaccine by intramuscular injection.

A method for treating and/or preventing a disease in a subject may comprise administering to the subject a vaccine according to any stabiliser formulation disclosed herein in an amount sufficient to treat or prevent the disease.

EXEMPLIFICATION

Preparation of Inactivated Yellow Fever Virus (YFV) Vaccine
Pre-Formulation Sub-Batch Creation For the initial clinical trial, three dose levels are planned. The Bulk Drug Substance is at the appropriate concentration for the high dose; the inactivated virus is in formulation buffer (target formulation: 10 mM Tris, 145-500 mM NaCl, pH 7.5). The final NaCl concentration will be dependent upon the dilution factor required to achieve the target potency of the Bulk Drug Substance. The Bulk Drug Substance is diluted ten fold with dilution buffer (10 mM Tris, 145 mM NaCl, pH 7.5) to prepare Sub-Batch M at the mid dose level. The Bulk Drug substance is diluted one hundred fold with dilution buffer to prepare Sub-Batch L at the low dose level. The remaining Bulk Drug Substance becomes the Sub-Batch H which is the starting material for the high dose material. All three sub-batches are stored in sterile PETG bottles at 2-8° C.
Adsorption to Alum Aluminum hydroxide is added to the Pre-Formulation Sub-batch in its PETG container to achieve an approximate final concentration of 0.2% in the Bulk Drug Product. One part of 2% Alhydrogel (Brenntag Biosector) is added to 8 parts of the Pre-Formulation Sub-batch. The sub-batch is thoroughly mixed for approximately 4 hours at 2-8° C. The alum-adsorbed sub-batch is then stored at 2-8° C. until excipient buffer addition. This is the Alum Formulated Inactivated Virus.
Qualification of Adsorption to Alum Qualification studies were performed to ensure complete adsorption of inactivated YFV by the alum. Tubes containing YFV in the presence or absence of 0.2% alum (final concentration) were mixed at 2-8° C. for ≥4 hr. The solutions containing YFV±alum mixtures were clarified by centrifugation at approximately 3000 rpm for 10 min at room temperature, and supernatant fluids were collected. The amount of YFV remaining in solution (not adsorbed) was measured using the 2E10 monoclonal ELISA assay for alum bound material. The amount of YF antigen in the control sample (no alum) was set as 100% and ELISA results obtained for the samples containing 0.2% alum were used to calculate the percent YFV antigen not adsorbed to alum. The results indicated that only 0.09% of the antigen was not bound to alum.

In addition a number of experiments were performed in an effort to show desorption of the YF virus antigen from alum under conditions that preserve the YF antigen. Neither high pH (pH 10) nor high salt (0.5M NaCl) were effective ways to desorb virus from the alum.
Addition of Excipients: Stabilization of the Alum Adsorbed Virus Bulk Upon completion of the alum formulation, excipients are added to stabilize the alum formulated, inactivated virus. The formulated virus is adjusted to an approximate final concentration of 10 mM Tris HCl, 145-500 mM NaCl, 12 mM $MgCl_2$, 100 mM glutamic acid, 1.1 mM mannitol, 20 mM trimethylamine-N-oxide, pH 7.5. A ten-fold concentrated solution of excipients is prepared with a target composition of 10 mM Tris HCl, 145 mM NaCl, 120 mM $MgCl_2$, 1000 mM glutamic acid, 11 mM mannitol, 200 mM trimethylamine-N-oxide, pH 7.5 One part of the 10× concentrated excipient solution is added to 9 parts of alum formulated, inactivated virus. The resulting suspension is mixed for ≥5 min at 2-8° C. to form the Bulk Drug Product which is stored at 2-8° C. until filling.

The bulk drug product is stored at 2 to 8° C. in PETG plastic bottles that are provided sterilised by gamma irradiation. The product contact surface of the plastic PETG bottles is comprised of polyethylene terephthalate glycol copolyester. Product contact surfaces in the bottles have been demonstrated to meet USP <88> Class VI standards.
Excipient Selection To optimize stability of the alum-adsorbed bulk, a design of experiments approach was used to screen various combinations of GRAS substances for their effects on the stability of YF virus under accelerated conditions, i.e. 37° C. Table 2.2.9 lists the five formulation conditions that produced the highest stability of virus compared to the no excipient control (10 mM Tris, 145 mM NaCl, pH 7.5).

Inactivated, alum-formulated YF virus containing 10 mM Tris, 145 mM NaCl, pH 7.5 was incubated at 37° C. for 12 days in the presence of the 5 different formulation mixtures (Table 2.2.9). The YF virus titer was determined on days 4, 7 and 12 using the 2E10 monoclonal ELISA format that measures alum-bound virus (Section 2.2.7.1.3); the titers for formulations containing excipient mixtures were compared to the titer of control sample containing NaCl-Tris HCl only.

The results are expressed as alum-ELISA Units. As shown in FIG. 1, formulation mixes 2 and 5 provided the highest stability at Day 12. The high concentration of mannitol made formulation mix 2 impractical; therefore formulation mix number 5 was selected as the basis for the final formulation. The FIGURE is a graph showing the stability of YF 17D virus adsorbed to alum in different formulation buffers, evaluated after 4, 7 and 12 days at 37° C. The YF titer measured by the 2E10 monoclonal ELISA, alum, is plotted for the five formulations tested. The formulations are indicated by number on the X-axis; the compositions are shown in the table below. The solid black bars represent the titer at 4 days of incubation, the gray bars represent the titer at 7 days of incubation and the diagonally hatched bars represent the titer at 12 days of incubation.

The table below lists only a few of the many formulation mixtures we tested for stabilisation of inactivated, alum-bound YF 17D virus.

TABLE 2.2.9

Formulation Mixtures Tested for Stabilization of Inactivated, Alum-bound YF 17D virus

| Formulation Mix ID | Components: |
|---|---|
| 1 | 8% 2-hydroxy propyl-beta-cyclodextrin, 0.05% Pluronic 68, 0.03 mg/mL Dextran sulfate, 8.2 mM Malic acid, pH 7.5 |
| 2 | 49 mM Glutamic acid, 137 mM Mannitol, 0.01 mg/mL Protamine, 0.02% Dextrose, pH 7.5 |
| 3 | 12.4 mM $MgCl_2$, 126.5 mM Glutamine, 0.2% Dextrose, pH 7.5 |
| 4 | 0.24% sorbitol, 455 mM Trimethylamine-N-oxide, 0.0004% Tween 80, 6.2 mM Glutamic acid, pH 7.5 |
| 5 | 11.8 mM $MgCl_2$, 94 mM Glutamic acid, 1.1 mM Mannitol, 18.7 mM Trimethylamine-N-oxide, pH 7.5 |

To investigate the effect of salt concentration in formulation mix number 5 on stability, inactivated, alum-formulated YF 17D virus containing 10 mM Tris, 11.8 mM $MgCl_2$, 94 mM Glutamic acid, 1.1 mM Mannitol, 18.7 mM Trimethylamine-N-oxide, pH 7.5 was incubated at 37° C. for 4 days in the presence of 150, 300, 500 and 700 mM NaCl. The control sample contained 10 mM Tris, 145 mM NaCl. YF virus titer was determined using the 2E10 monoclonal ELISA format that measures alum-bound virus. Alum-formulated YF virus was most stable at 150 mM NaCl. As measured by retention of the 2E10 epitope, the stability of the formulated, inactivated alum bound virus decreased as the salt concentration increased. Based on these data, a range of 145-500 mM NaCl was determined to provide an acceptable stability profile for the final formulation.

In another example, a beta-propiolactone (BPL) inactivated whole virion vaccine adsorbed to aluminum hydroxide ("alum") adjuvant was prepared. The vaccine, provided as a suspension for injection to be administered by intramuscular injections, was manufactured from YF 17D strain grown in continuous African green monkey kidney (Vero) cell culture. The virus was harvested from Vero cell culture fluid, purified by depth filtration, ultrafiltration, inactivated with beta-propiolactone (BPL), further purified by chromatography, adsorbed to aluminum hydroxide adjuvant and formulated with stabilisers according to an embodiment of the invention. The vaccine was formulated to contain 0.2% alum, 10 mM Tris HCl, 145-500 mM NaCl, 1.2 mM MgCl2, 10 mM glutamic acid, 0.11 mM mannitol, 2.0 mM trimethylamine-N-oxide; pH 7.5.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed:

1. A formulation capable of enhancing thermostability and shelf-life of a biological product, the formulation comprising: trimethylamine-N-oxide, mannitol, glutamic acid, magnesium chloride, ($MgCl_2$), a physiologically acceptable buffer, a pharmaceutically acceptable carrier, and optionally, sodium chloride; wherein the concentration of trimethylamine-N-oxide is from about 1.5 millimolar to about 800 millimolar; the concentration of magnesium chloride is from about 0.8 millimolar to about 80 millimolar; the concentration of glutamic acid is from about 5 millimolar to about 500 millimolar; the concentration of mannitol, ($C_6H_8(OH)_6$), is from about 0.01 percent (w/v) to about 5 percent (w/v); wherein when sodium chloride is present, the concentration of sodium chloride is from about 100 millimolar to about 500 millimolar;
wherein the biological product is a vaccine comprising an inactivated or an attenuated Yellow Fever virus.

2. The formulation of claim 1, wherein the concentration of trimethylamine-N-oxide is from about 2.0 millimolar to about 500 millimolar.

3. The formulation of claim 2, wherein the concentration of magnesium chloride, $MgCl_2$, is from about 1 millimolar to about 12 millimolar.

4. The formulation of claim 3, wherein the concentration of glutamic acid is from about 8 millimolar to about 200 millimolar.

5. The formulation of claim 4, wherein the concentration of mannitol, ($C_6H_8(OH)_6$), is from about 0.05 millimolar to about 2 millimolar.

6. The formulation of claim 1, wherein the physiologically acceptable buffer is present in an amount effective to adjust or maintain the pH at from about 6.5 to about 8.5.

7. The formulation of claim 6, wherein the physiologically acceptable buffer is present in an amount effective to adjust or maintain the pH at about 7.5.

8. The formulation of claim 1, wherein the buffer is a tris buffer or a phosphate buffer.

9. A vaccine preparation comprising the Yellow Fever virus formulation of claim 1.

10. A vaccine comprising an inactivated or attenuated Yellow Fever virus, an adjuvant, and a stabilizer comprising from about 1 millimolar to about 50 millimolar magnesium chloride, ($MgCl_2$); from about 8 millimolar to about 200 millimolar glutamic acid; from about 0.05 millimolar to about 2.5 millimolar mannitol; from about one millimolar to about 500 millimolar trimethylamine-N-oxide; and an amount of a physiologically acceptable buffer effective to adjust or maintain the pH at from about 6.5 to about 8.5.

11. A formulation capable of enhancing thermostability and shelf-life of a biological product, the formulation comprising: from about one millimolar to about 200 millimolar glutamic acid, from about 0.05 millimolar to about 5 millimolar mannitol, from about 0.01 milligram per milliliter to about 0.1 milligram per milliliter protamine, and from about 0.01 percent to about 1 percent dextrose, and an amount of a physiologically acceptable buffer effective to adjust or maintain the pH at from about 6.5 to about 8.5; wherein the biological product is a vaccine comprising an inactivated or attenuated Yellow Fever virus.

12. A formulation comprising: an inactivated or an attenuated Yellow Fever virus; alum; trimethylamine-N-oxide; mannitol; glutamic acid; magnesium chloride, ($MgCl_2$); sodium chloride; and a suitable buffer to maintain the pH of the formulation at about 7.5, wherein the formulation comprising from about 0.1 percent (w/v) to about 0.5 percent (w/v) alum; from about 1.5 millimolar to about 20 millimolar trimethylamine-N-oxide; from about 0.05 millimolar to about 2 millimolar mannitol; from about 8 millimolar to about 150 millimolar glutamic acid; and from about 100 millimolar to about 500 millimolar sodium chloride.

13. The formulation of claim 12, comprising about 0.2 percent (w/v) alum; about 2 millimolar trimethylamine-N-oxide; from about 0.10 millimolar to about 0.20 millimolar mannitol; about 10 millimolar glutamic acid; and from about 145 millimolar to about 500 millimolar sodium chloride.

14. A method for stabilizing a Yellow Fever virus vaccine comprising adding to the vaccine an amount of a formulation according to claim 1, effective to stabilize the vaccine.

15. A method for administering the vaccine of claim 1, the method comprising administering the vaccine by intramuscular injection.

16. A method for treating and/or preventing a Yellow Fever virus disease in a subject, the method comprising administering to the subject the vaccine of claim 1, in an amount sufficient to treat or prevent the disease.

* * * * *